(12) United States Patent
Niwa

(10) Patent No.: US 7,608,176 B2
(45) Date of Patent: Oct. 27, 2009

(54) GAS CONCENTRATION DETECTING APPARATUS

(75) Inventor: Mitsunobu Niwa, Kariya (JP)

(73) Assignee: DENSO Corporation, Kariya (JP)

( * ) Notice: Subject to any disclaimer, the term of this patent is extended or adjusted under 35 U.S.C. 154(b) by 637 days.

(21) Appl. No.: 10/681,138

(22) Filed: Oct. 9, 2003

(65) Prior Publication Data
US 2004/0074773 A1 Apr. 22, 2004

(30) Foreign Application Priority Data
Oct. 10, 2002 (JP) ............................. 2002-297772

(51) Int. Cl.
*G01N 27/407* (2006.01)
(52) U.S. Cl. .................. 204/406; 204/425; 205/781
(58) Field of Classification Search .............. 204/406, 204/424, 425, 426; 205/781, 785; 73/23.31
See application file for complete search history.

(56) References Cited

U.S. PATENT DOCUMENTS

| 4,777,922 | A | * | 10/1988 | Mieno et al. ................ 123/688 |
| 4,808,269 | A | * | 2/1989 | Kawanabe et al. .......... 205/785 |
| 5,340,462 | A |   | 8/1994 | Suzuki |
| 6,120,677 | A |   | 9/2000 | Yamada et al. |
| 6,290,840 | B1 | * | 9/2001 | Kato et al. ............... 205/784.5 |
| 6,347,544 | B1 |   | 2/2002 | Hada et al. |
| 6,453,724 | B1 |   | 9/2002 | Kawase et al. |
| 2002/0104758 | A1 | * | 8/2002 | Mizutani et al. ............ 204/427 |

FOREIGN PATENT DOCUMENTS

| JP | 1-227835 | 9/1989 |
| JP | 6-11482 | 1/1994 |
| JP | 10-73565 | 3/1998 |
| JP | 11-6813 | 1/1999 |
| JP | 2000-171439 | 6/2000 |
| JP | 2002-372514 | 12/2002 |

OTHER PUBLICATIONS

JPO Examination Report dated Aug. 1, 2006.

* cited by examiner

*Primary Examiner*—Kaj K Olsen
(74) *Attorney, Agent, or Firm*—Nixon & Vanderhye P.C.

(57) ABSTRACT

The present invention relates a gas concentration detecting apparatus capable of appropriately making a decision on activation of each of a pump cell, a monitor cell and a sensor cell of its gas concentration sensor. In the apparatus, a control circuit outputs an oxygen concentration value on the basis of a current flowing when a voltage is applied to the pump cell and outputs an NOx concentration value on the basis of a current flowing at the voltage application to the sensor cell. Moreover, the control circuit separately makes a decision on activation of the pump cell and a decision on activation of the sensor cell in the middle of the activation of the sensor. Still moreover, the control circuit makes the decision on the activation of the sensor cell after the activation of the pump cell reaches completion.

15 Claims, 9 Drawing Sheets

GAS CONCENTRATION DETECTING APPARATUS

BACKGROUND OF THE INVENTION

1) Field of the Invention

The present invention relates to a gas concentration detecting apparatus made to detect a concentration of an oxygen concentration and specific gas component of a gas to be detected through the use of a gas concentration sensor for outputting an oxygen concentration signal and a specific gas concentration signal in the basis of the detection results.

2) Description of the Related Art

As such a type of gas concentration detecting apparatus, there has known an apparatus which detects NOx (nitrogen oxides) of an exhaust gas from, for example, a vehicle engine through the use of a limiting-current type gas concentration sensor. The gas concentration sensor has, for example, a three-cell construction including a pump cell, a sensor cell and a monitor cell, and in the pump cell, oxygen of an exhaust gas introduced into a chamber is pumped in and out and the oxygen concentration of the exhaust gas is detected at the same time. Moreover, the sensor cell detects the NOx concentration (concentration of a specific gas component) of the gas after passed through the pump cell, and the monitor cell detects the concentration of the residual oxygen of the in-chamber gas after passed through the pump cell.

The above-mentioned gas concentration sensor can acquire a normal oxygen concentration signal on the condition that the pump cell is in a predetermined active state, and can acquire a normal NOx concentration signal on the condition that the sensor cell is in a predetermined active state. Therefore, in general, the resistance value (for example, element impedance) of a solid electrolyte element forming each of the cells is detected and activation control is implemented through the energizing to a heater (supply of power to a heater) so that the element impedance reaches a target (desired) value corresponding to the active temperature. For example, with respect to the sensor cell, the element impedance is detected, and the energizing to a heater is feedback-controlled on the basis of a deviation between the element impedance detection value and a target value (for example, see Japanese Patent Laid-Open No. 2000-171439).

However, in the case of the existing technique, a decision on the completion of activation of the pump cell and a decision on the completion of activation of the sensor cell are made at the same time regardless of the actual degree of activation of each cell. For this reason, by the time the oxygen concentration signal or the NOx concentration signal meets the requirements for the engine control or the like, there may be a need to wait for approximately several minutes after the start-up of the sensor. This creates a problem in that the requirement for the sensor output to be available in early stages does not reach satisfaction.

SUMMARY OF THE INVENTION

The present invention has been developed with a view to eliminating this problem, and it is therefore an object of the invention to provide a gas concentration detecting apparatus capable of making an appropriate decision on the completion of activation of each cell to permit the oxygen concentration signal or the specific gas concentration signal to be used at an optimum timings.

For this purpose, in a gas concentration detecting apparatus according to the present invention, an oxygen concentration signal is outputted on the basis of a current flowing when a voltage is applied to a first cell, and a specific gas concentration signal is outputted on the basis of a current flowing when a voltage is applied to a second cell. In particular, according to a first aspect of the present invention, a decision on activation (activated state) of the first cell and a decision on activation of the second cell are separately made in the middle of activation of a gas concentration sensor, and a decision indicative of the activation of the second cell is made after a decision is made that the activation of the first cell reaches completion. In this case, according to a second aspect of the present invention, a first cell electrode provided in a chamber is a specific-gas inactive electrode inactive in a specific gas component, while a second cell electrode provided in the same chamber is a specific-gas active electrode active in the specific gas component.

In short, in the aforesaid gas concentration sensor, a normal signal output is obtainable under an activated condition and it is essential to make a decision on activation. At this time, in comparison between the first cell and the second cell, the times needed for their activation are different from each other, and the first cell is activated earlier (the first cell reaches activation completion earlier). That is, in a case in which the activation starts at the initial state (cold state) of the gas concentration sensor, the surplus oxygen in the chamber is discharged by the first cell and, when the residual oxygen concentration in the chamber reaches a predetermined level, the detection current by the first cell becomes normal at that time and, hence, a decision can be made that the activation of the first cell reaches completion. On the other hand, the present inventor has confirmed that, in the second cell, oxygen adsorbs onto an electrode (a specific-gas active electrode, such as rhodium) constituting the second cell while the sensor is in the stopping condition and the time needed for discharging the adsorbed oxygen is approximately several minutes (although the oxygen adsorption also occurs in the first cell electrode forming a specific-gas inactive-electrode, the adsorption amount is small). Therefore, even if the activation of the first cell reaches completion, the activation of the second cell does not reach completion yet, and the second cell reaches activation completion thereafter. According to the present invention, the activation decision is individually made for each cell, which enables an appropriate decision on the activation of each cell and permits the oxygen concentration signal or the specific gas concentration signal to be used at the optimum time. In particular, with respect to the first cell, the decision on the activation completion can be made without waiting for the activation completion of the second cell and, hence, the normal oxygen concentration signal is available in early stages.

According to a third aspect of the present invention, the gas concentration sensor includes a third cell for detecting a residual oxygen concentration of a gas passing through the first cell so that the voltage to be applied to the first cell is variably controlled on the basis of a detection result in the third cell. With this construction, the residual oxygen concentration in the chamber is controllable with high accuracy.

According to a fourth aspect of the present invention, a resistance value of a solid electrolyte element of any one of the cells is detected through the use of element resistance detecting means and the control on the element activation is implemented so that the detected element resistance value is kept at a predetermined target value. Moreover, the transition of the element resistance value detected by the element resistance detecting means is monitored in the middle of the activation of the gas concentration sensor, and when the element resistance value reaches an activation decision value based upon the target value, a decision is made that the first cell reaches its activation. The activation decision value can be set at a value equal to the target value or it can also be set at a value obtained in the middle of the activation prior to the arrival at the target value. With this arrangement, with respect to the first cell, the normal oxygen concentration signal becomes attainable in early stages.

The activation speed of the first cell shows a different value for each gas concentration sensor. Therefore, according to a fifth aspect of the present invention, when the element resistance value detected by the element resistance detecting means in the middle of the activation of the gas concentration sensor reaches the activation decision value and a predetermined period of time elapses after the detected element resistance value reaches the activation decision value, a decision is made that the first cell reaches the activation. Alternatively, according to a sixth aspect of the present invention, when the element resistance value detected by the element resistance detecting means in the middle of the activation of the gas concentration sensor reaches the activation decision value and the detection current by the first cell falls within a predetermined range, a decision is made that the first cell reaches the activation. These arrangements can enhance the accuracy of the activation decision.

In addition, according to a seventh aspect of the present invention, when a predetermined period of time elapses after the start of the heater energizing control in the middle of the activation of the gas concentration sensor, a decision is made that the first cell reaches the activation. Also with this arrangement, with respect to the first cell, a normal oxygen concentration signal is obtainable in early stages.

Still additionally, according to an eighth aspect of the present invention, an elapsed time after the decision is made that the first cell reaches the activation is measured and, when the elapsed time reaches a predetermined time, a decision is made that the second cell reaches the activation. With this arrangement, a decision on the activation completion of the second cell becomes feasible at an appropriate time after the completion of the activation of the first cell.

Moreover, the activation speed of the second cell shows a different value for each gas concentration sensor. Therefore, according to a ninth aspect of the present invention, when an elapsed time reaches a predetermined time after the first cell reaches activation and the detection current by the second cell falls within a predetermined range, a decision is made that the second cell reaches activation. Alternatively, when an elapsed time reaches a predetermined time after the first cell reaches activation and the detection current by the third cell falls within a predetermined range, a decision is made that the second cell reaches activation. These arrangements can improve the accuracy of the activation decision.

Still moreover, the predetermined time is determined on the basis of a time needed for discharging all the oxygen adsorbed onto the specific-gas active electrode of the second cell.

BRIEF DESCRIPTION OF THE DRAWINGS

Other objects and features of the present invention will become more readily apparent from the following detailed description of the preferred embodiments taken in conjunction with the accompanying drawings in which.

DESCRIPTION OF THE PREFERRED EMBODIMENTS

An embodiment of the present invention will be described hereinbelow with reference to the drawings.

A gas concentration detecting apparatus according to the embodiment is applied to, for example, a car engine, and is designed to use a limiting-current type gas concentration sensor to detect an oxygen concentration and a specific gas component concentration in an exhaust gas to be detected.

Figure 2A:
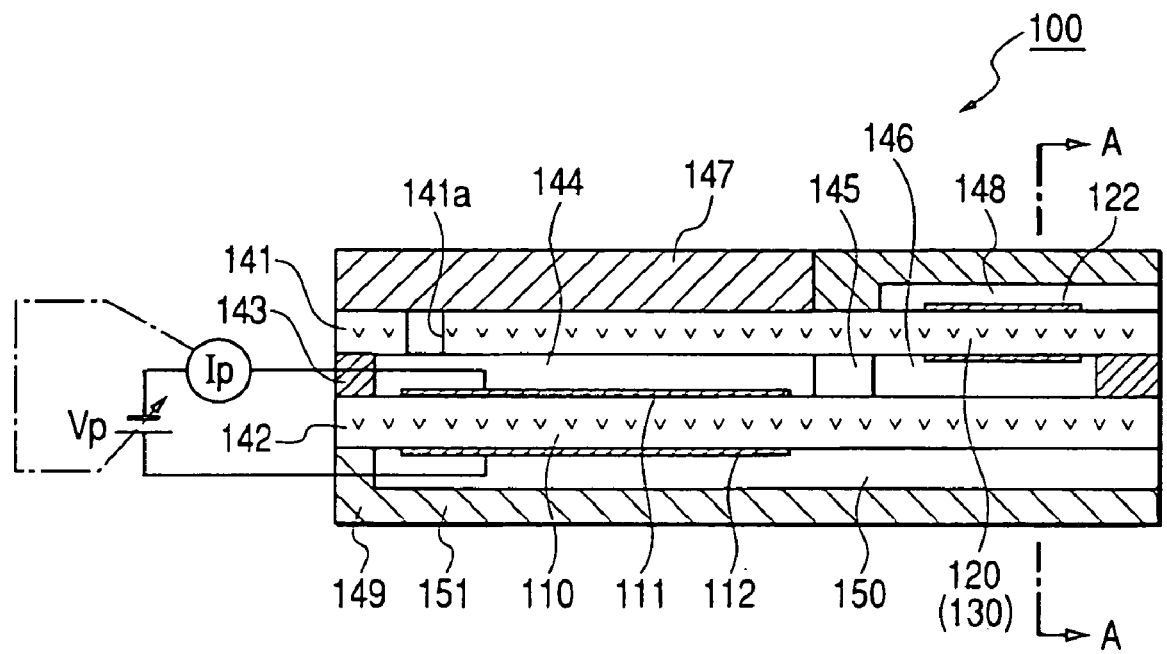
FIGS. 2A and 2B are cross-sectional views showing a construction of a gas concentration sensor according to the embodiment.
Figure 2B:
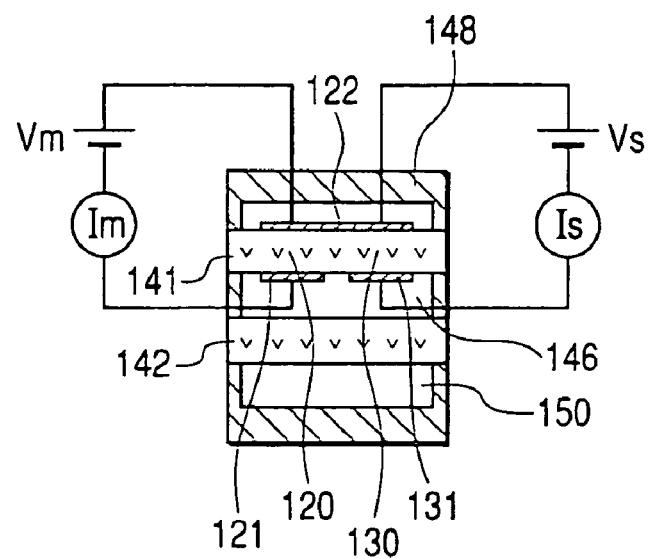

First of all, referring to FIGS. 2A and 2B, a description will be given hereinbelow of a construction of a gas concentration sensor of the gas concentration detecting apparatus according to the embodiment. The gas concentration sensor, shown in FIGS. 2A and 2B and generally designated at reference numeral 100, has a three-cell construction comprising a pump cell forming a "first cell", a sensor cell forming a "second cell" and a monitor cell forming a "third cell". This gas concentration sensor is employed as a so-called compound gas sensor capable of simultaneously detecting an oxygen concentration and an NOx concentration in an exhaust gas. Incidentally, since the monitor cell has a function to discharge oxygen of a gas as well as the pump cell, it can also be referred to as a "second pump cell". FIG. 2A is a cross-sectional view showing a structure of a tip portion of a sensor element and FIG. 2B is a cross-sectional view taken along a line A-A of FIG. 2A.

In the gas concentration sensor 100, each of solid electrolytes (solid electrolyte elements) 141 and 142 made of an oxygen ion conductive material is formed into a sheet-like configuration, and they are stacked to be separated by a predetermined spacing in a vertical direction in the illustrations in a state where a spacer 143 made of an insulating material such as alumina is interposed therebetween. A pinhole 141a is made in the upper-side solid electrolyte 141 so that an exhaust gas existing around the sensor 100 is introduced through the pinhole 141a into a first chamber 144. The first chamber 144 communicates through a restriction portion 145 with a second chamber 146. In the illustrations, reference numeral 147 represents a porous diffusive layer.

On the lower-side solid electrolyte 142, a pump cell 110 is provided to confront the first chamber 144, and the pump cell 110 has a function to discharge or take in (pump) oxygen of an exhaust gas introduced into the first chamber 144 and further has a function to detect an oxygen concentration of the exhaust gas at the oxygen pumping. In this case, the pump cell 110 includes a pair of upper and lower electrodes 111 and 112 in a state where the solid electrolyte 142 is interposed therebetween and, of these, the first chamber 144 side electrode 111 serves as a NOx inactive electrode (which is an electrode is weak in decomposing an NOx gas). The pump cell 110 decomposes oxygen existing in the first chamber 144 and discharges it through the electrode 112 to an atmosphere passage 150 side.

In addition, on the upper-side solid electrolyte 141, a monitor cell 120 and a sensor cell 130 are provided to confront the second chamber 146. The monitor cell 120 generates an electromotive force in accordance with a residual oxygen concentration in the second chamber 146 or generates a current output in response to a voltage being applied thereto. The sensor cell 130 detects an NOx concentration of a gas after passing through the pump cell 110.

In particular, according to this embodiment, as shown in FIG. 2B, the monitor cell 120 and the sensor cell 130 are disposed in parallel with each other to be positioned equivalently with respect to a flow direction of the exhaust gas, and an atmosphere passage 148 side electrode of each of the cells 120 and 130 serves as a common electrode 122. That is, the monitor cell 120 is composed of the solid electrolyte 141, an electrode 121 and the common electrode 122, with the electrode 121 and the common electrode 122 being disposed in opposed relation to each other in a state where the solid electrolyte 141 being interposed therebetween. Likewise, the sensor cell 130 is composed of the solid electrolyte 141, an electrode 131 and the common electrode 122, with the electrode 131 and the common electrode 122 being disposed in opposed relation to each other in a state where the solid electrolyte 141 is interposed therebetween. The electrode 121 (second chamber 146 side electrode) of the monitor cell 120 is made of a noble metal such as Au—Pt inactive in an NOx gas, while the electrode 131 (second chamber 146 side electrode) of the sensor cell 130 is made of a noble metal such as platinum (Pt), rhodium (Rh) or the like active in an NOx gas.

Figure 3A:
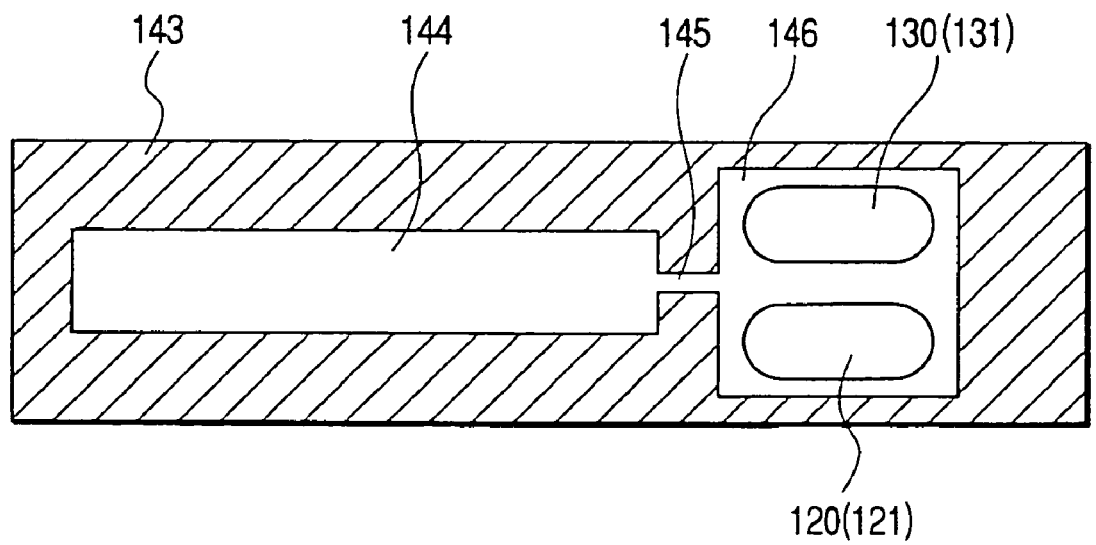
FIGS. 3A and 3B are plan cross-sectional views showing locations of electrodes of a monitor cell and a sensor cell according to the embodiment.
Figure 3B:
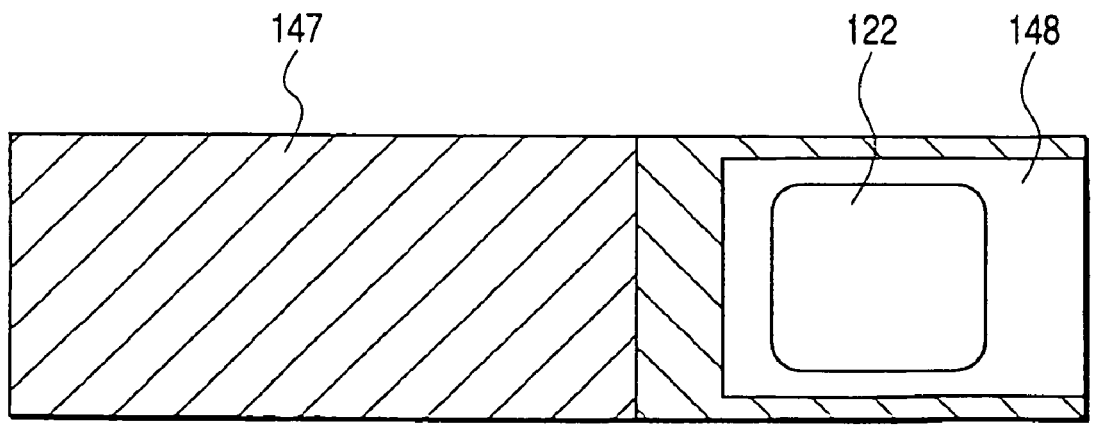

FIG. 3A is a plan cross-sectional view showing electrodes of the monitor cell 120 and the sensor cell 130, viewed from the second chamber 146 side, and FIG. 3B is a plan cross-sectional view showing the electrodes of these cells 120 and 130, viewed from the atmosphere passage 148 side.

With this construction, the exhaust gas introduction distances in the monitor cell 120 and the sensor cell 130 becomes equal to each other. In consequence, the sensitivities of the monitor cell 120 and the sensor cell 130 with respect to the residual oxygen after passing through the pump cell 110 becomes equal to each other, which enables a high-accuracy detection of gas concentration. However, in addition to being disposed in parallel along an exhaust gas flowing direction as shown in FIG. 3A, the electrodes of the monitor cell 120 and the sensor cell 130 can also be disposed in front and in rear (that is, right side and left side in the illustration) in the exhaust gas flowing direction. For example, the monitor cell 120 is located on the upstream side (left side in the illustration) and the sensor cell 130 is located on the downstream side (right side in the illustration). Moreover, the use of the common electrode 122 for each cell is not essential but the employment of separate electrodes is also feasible.

An insulating layer 149 is placed on a lower surface of the solid electrolyte 142, and this insulating layer 149 establishes the atmosphere passage 150. Moreover, in the insulating layer 149, a heater 151 is buried which heats the entire sensor 100. The heater 151 generates thermal energy in accordance with power supply from the external to place the entire sensor 100 including the pump cell 110, the monitor cell 120 and the sensor cell 130 into an activated state.

In the gas concentration sensor 100 thus constructed, an exhaust gas is introduced through the porous diffusive layer 147 and the pinhole 141a into the first chamber 144. Moreover, when a voltage Vp is applied between the pump cell electrodes 111 and 112 at the time that the exhaust gas passes in the vicinity of the pump cell 110, a decomposition reaction occurs, and the oxygen is taken in and out through the pump cell 110 in accordance with an oxygen concentration in the first chamber 144. At this time, since the first chamber 144 side electrode 111 is inactive in NOx, the NOx is not decomposed in the pump cell 110, and only oxygen is decomposed and discharged to the atmosphere passage 150. Moreover, an oxygen concentration contained in the exhaust gas is detected on the basis of a current (pump cell current Ip) flowing through the pump cell 110.

After passing through in the vicinity of the pump cell 110, the exhaust gas flows into the second chamber 146, and the monitor cell 120 generates an output corresponding to a residual oxygen concentration of the gas. The output of the monitor cell 120 is detected as a monitor cell current Im in a manner such that a predetermined voltage Vm is applied between the monitor cell electrodes 121 and 122. Moreover, NOx of the gas is reduction-decomposed when a predetermined voltage Vs is applied between the sensor cell electrodes 131 and 122 and the oxygen generated at that time is discharged to the atmosphere passage 148. At this time, the concentration of an NOx contained in the exhaust gas is detected on the basis of a current (sensor cell current Is) flowing in the sensor cell 130.

In the pump cell 110, the voltage Vp to be applied is variably controlled in accordance with an oxygen concentration (that is, the pump cell current Ip) of the exhaust gas in each case. As one example, through the use of an applied voltage map produced on the basis of a limiting-current characteristic of the pump cell 110, the voltage Vp to be applied is controlled on the basis of the pump cell current Ip in each case. Thus, the applied-voltage control is implemented so that the voltage to be applied is shifted to the high voltage side as the oxygen concentration of the exhaust gas becomes higher. It is also appropriate that the voltage Vp to be applied is feedback-controlled so that the residual oxygen concentration in the second chamber 146 becomes constant (in other words, the monitor cell current Im becomes constant). Through the above-mentioned control, the oxygen of the exhaust gas introduced into the first chamber 144 is instantaneously discharged so that the residual oxygen concentration after the oxygen discharge is maintained at a desired low concentration level.

Meanwhile, in the above-described gas concentration sensor 100, after the surplus oxygen of the exhaust gas is discharged by the pump cell 110, a gas containing given residual oxygen is fed to the monitor cell 120 and the sensor cell 130. Moreover, in the monitor cell 120, the monitor cell current Im is measured according to the residual oxygen concentration of the gas, while in the sensor cell 130, the sensor cell current Is is measured according to the NOx concentration of the gas. At this time, preferably, in the sensor cell 130, only the NOx of the gas is reduction-decomposed and a current value is measured accordingly. However, in fact, a current component according to a residual oxygen (minute oxygen quantity) of the gas is additionally measured. That is, the sensor cell current Is measured includes a portion corresponding to an NOx reaction and a portion corresponding to a residual oxygen reaction and, of these, the portion corresponding to the residual oxygen reaction becomes an offset error. In this embodiment, for removing a portion corresponding to the offset error from the sensor cell current Is, the monitor cell current Im is subtracted from the measured sensor cell current Is and an NOx concentration output is obtained on the basis of the difference (Is−Im) therebetween. For convenience only, in the following description, the (Is−Im) value is referred to as an "NOx detection current".

Secondly, referring to FIG. 1, a description will be given hereinbelow of an electrical arrangement of the gas concentration detecting apparatus according to this embodiment. Although FIG. 1 shows a gas concentration detecting apparatus using the above-described gas concentration sensor 100, for convenience only, in the illustration the electrodes of the monitor cell 120 and the sensor cell 130 are located in a state arranged horizontally.

Figure 1:
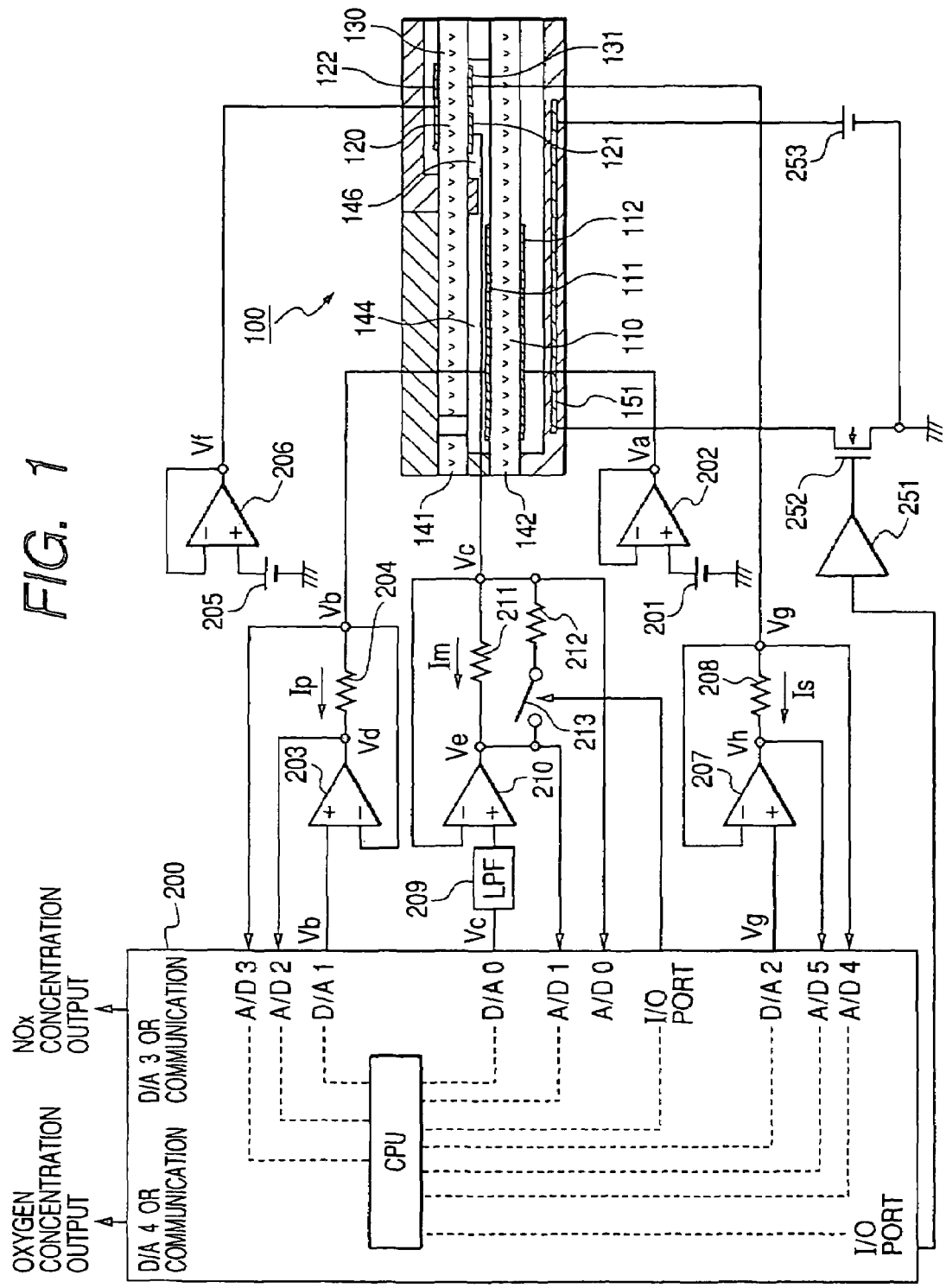
FIG. 1 is an illustration of a configuration of a gas concentration detecting apparatus according to an embodiment of the present invention.

In FIG. 1, a control circuit 200 is equipped with a well-known microcomputer including a CPU, A/D converters, D/A converters, I/O ports and other components, and is made to properly output a voltage to be applied to each of the cells 110 to 130 through the corresponding D/A converter (D/A 0, D/A 1, D/A 2). Moreover, the control circuit 200 takes in the voltage at terminals Vc, Ve, Vd, Vb, Vg and Vh through the A/D converters (A/D 0 to A/D 5) for measuring currents flowing in the cells 110 to 130. Still moreover, the control circuit 200 detects an oxygen concentration (A/F) or an NOx concentration on the basis of the measurement current in the pump cell 110 or the sensor cell 130 and outputs the detection values through the D/A converter (D/A 4, D/A 3) to the external.

A detailed description will be given hereinbelow of the circuit arrangement. In the pump cell 110, a reference voltage Va produced by a reference power supply source 201 and an operational amplifier 202 is applied to one electrode 112 while an instruction voltage Vb from the control circuit 200 is applied through an operational amplifier 203 and a current detecting resistor 204 to the other electrode 111. When a current flow in the pump cell 110 in accordance with an oxygen concentration of an exhaust gas at the application of the instruction voltage Vb, the current detecting resistor 204 detects that current. That is, the voltages Vb and Vd at both the terminals of the current detecting resistor 204 are inputted to the control circuit 200 so that a pump cell current Ip is calculated on the basis of these voltages Vb and Vd.

In addition, a reference voltage Vf produced by a reference power supply source 205 and an operational amplifier 206 is applied to the common electrode 122 of the monitor cell 120 and the sensor cell 130, while an instruction voltage Vg from the control circuit 200 is applied through an operational amplifier 207 and a current detecting resistor 208 to the sensor cell electrode 131 different from the common electrode 122. When a current flow in the sensor cell 130 in accordance with an NOx concentration of the gas at the application of the instruction voltage Vg, the current detecting resistor 208 detects that current. That is, the voltages Vg and Vh at both the terminals of the current detecting resistor 208 are inputted to the control circuit 200 so that a sensor cell current Is is calculated on the basis of these voltages Vg and Vh.

Still additionally, an instruction voltage Vc from the control circuit 200 is applied through an LPF (Low Pass Filter) 209, an operational amplifier 210 and a current detecting resistor 211 to the monitor cell electrode 121 different from the common electrode 122. When a current flows in the monitor cell 120 in accordance with a residual oxygen concentration of the gas at the application of the instruction voltage Vc, the current detecting resistor 211 detects that current. That is, the voltages Vc and Ve at both the terminals of the current detecting resistor 211 are inputted to the control circuit 200 so that a monitor cell current Im is calculated on the basis of these voltages Vc and Ve. The LPF 209 is realizable with a primary filter comprising, for example, a resistor and a capacitor.

Yet additionally, in this embodiment, the so-called sweep method is put to use and an element admittance is detected as an "element resistance value" in the monitor cell 120. That is, at the detection of the admittance of the monitor cell 120, the control circuit 200 switches a monitor cell applied voltage (instruction voltage Vc) to at least one of the positive and negative sides in an instant (for example, within a time of approximately several tens to 100 μsec). This applied voltage is applied to both the electrodes of the monitor cell 120 while being attempered through the LPF 209 into a sine wave. It is preferable that the frequency of the alternating-current voltage exceeds 10 kHz, and the time constant of the LPF 209 is set at approximately 5 μsec. The element admittance of the monitor cell 120 is calculated on the basis of a voltage variation and a current variation (admittance=current variation/voltage variation).

In this connection, it is also appropriate to use, in place of the element admittance, an element impedance which is a reciprocal of the element admittance as the element resistance value. Moreover, it is also acceptable to employ, in place of the detection of the admittance (or the impedance) of the monitor cell 120, the detection of the admittance (or the impedance) of the pump cell 110 or the detection of the admittance (or the impedance) of the sensor cell 130.

In the monitor cell 120 and the sensor cell 130, the one electrodes are placed in the form of a common electrode, which provides an advantage in the reduction of a reference voltage side drive circuit and an advantage of the decrease in the number of takeout lead wires from the gas concentration sensor 100. Moreover, since the monitor cell 120 and the sensor cell 130 are formed using the same solid electrolyte 141 in a state adjacent to each other, although there is a possibility that a current flow in the adjacent electrode at the sweep so that the admittance (element resistance) detection accuracy comes down, the employment of the common electrode 122 makes one electrodes equal in electric potential, which lessens the influence thereof.

In addition, in the monitor cell 120, a current of approximately several μA flows at the detection of a residual oxygen concentration while a current of approximately several mA flow at the sweep for the admittance detection. If the currents on different orders are detected through the use of the same detection resistance, an overrange occurs, or the detection accuracy deteriorates. For this reason, in this embodiment, the current detection resistance is switched between the residual oxygen detection and the admittance detection by the monitor cell 120. Concretely, another current detecting resistor 212 and a switch circuit 213 (for example, semiconductor switch) are provided in parallel with the current detecting resistor 211. The switch circuit 213 is turned on/off in accordance with an output from the I/O port of the control circuit 200. In this case, at the normal gas concentration detection, the switch circuit 213 is turned off (opened) and a monitor cell current Im is detected through the use of the current detecting resistor 211 having a resistance of approximately several hundreds kΩ. On the other hand, at the detection of the admittance, the switch circuit 213 is turned on (closed) and a monitor cell current Im is detected through the use of the current detecting resistors 211 and 212 which provide several hundreds Ω.

Moreover, the CPU of the control circuit 200 outputs a control instruction value Duty through the I/O port to operate a MOSFET driver 251. At this time, the power to be supplied from a power supply source 253 (for example, a battery power source) to the heater 151 is PWM-controlled by a MOSFET 252.

Figure 4:
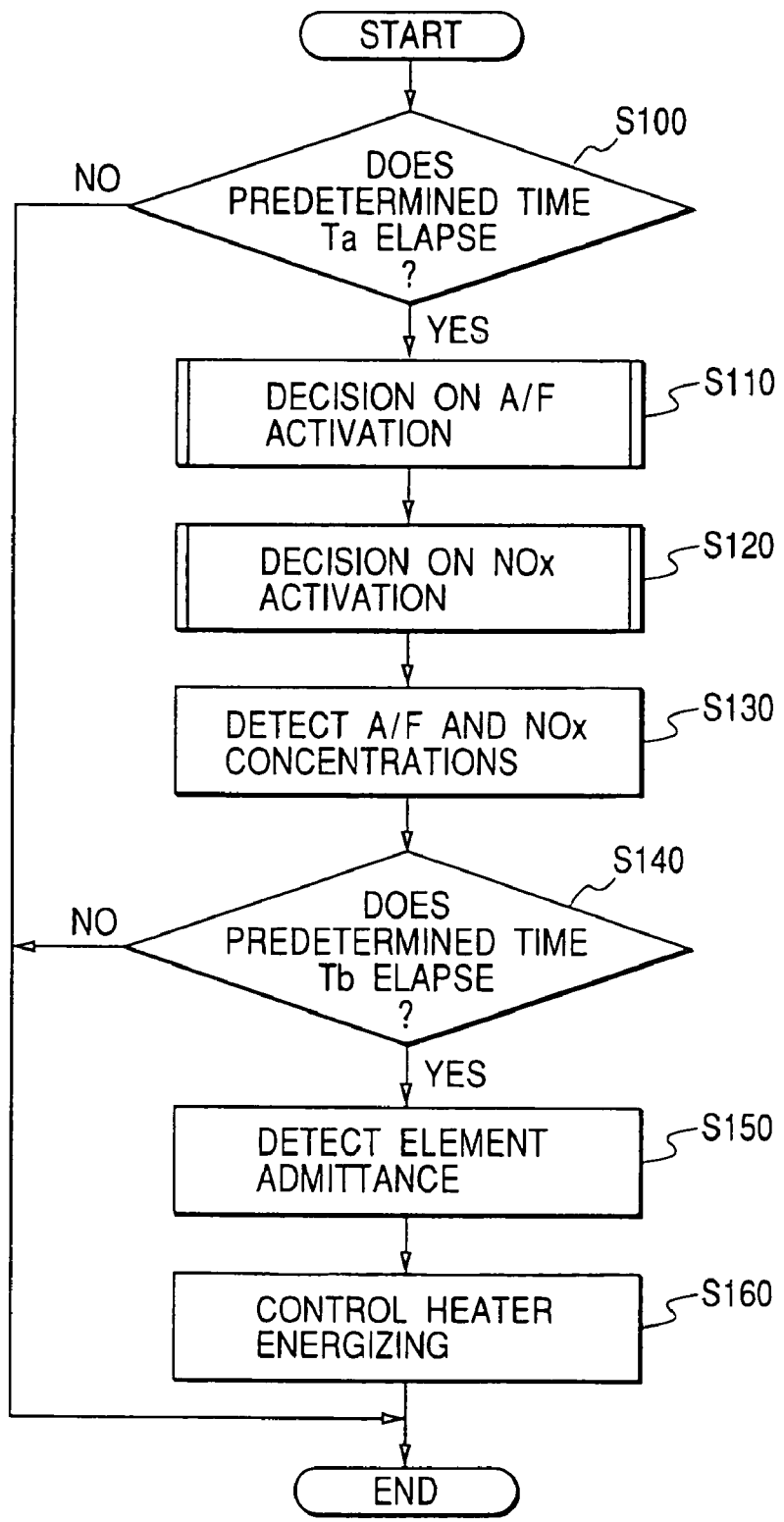
FIG. 4 is a flow chart showing a main routine according to the embodiment.

Furthermore, a description will be given hereinbelow of an operation of the gas concentration detecting apparatus thus constructed. FIG. 4 is a flow chart showing the outline of a main routine to be executed in the control circuit 200. This routine starts in response to the power-on for the control circuit 200.

In FIG. 4, a step S100 is first implemented to make a decision as to whether or not a predetermined time Ta has elapsed from the last detection of A/F (oxygen concentration) and NOx concentration. The predetermined time Ta corresponds to a period of detection of the A/F and NOx concentration, and for example, it is set at Ta=4 msec. If the answer of the step S100 indicates "YES", a step S110 follows to implement the A/F activation decision processing and a step S120 further follows to conduct the NOx activation decision processing. The A/F activation decision is for making a decision as to whether or not to provide a normal A/F output since the pump cell 110 reaches the activation completion, and the NOx activation decision is for making a decision as to whether or not to provide a normal NOx concentration output since the sensor cell 130 reaches the activation completion. These activation decisions will be mentioned in detail later.

Thereafter, a step S130 is implemented to conduct the A/F and NOx concentration detection processing. In the A/F (oxygen concentration) detection processing, there is set a pump cell applied voltage according to a pump cell current Ip in each case and there is inputted an A/D value of the pump cell current Ip measured at the voltage application. Moreover, the pump cell current Ip inputted is converted into an A/F value. In the NOx concentration detection processing are set a predetermined sensor cell applied voltage and inputted an A/D value of a sensor cell current Is measured at the voltage application, and further set a predetermined monitor cell applied voltage and inputted an A/D value of a monitor cell current Im measured at the voltage application. Moreover, The monitor cell current Im is subtracted from the sensor cell current Is, and the NOx detection current (Is−Im), which is a difference value therebetween, is converted into an NOx concentration value. These A/F value and NOx concentration value are properly outputted to an engine ECU (not shown) or the like.

After the detection of the A/F and the NOx concentration, in a step S140, a decision is made as to whether or not a predetermined time Tb has elapsed from the detection of the last element admittance. The predetermined time Tb corresponds to a period of detection of the element admittance, and for example, 129 msec, 2 sec or other time is selectively set in accordance with an engine operating condition. Moreover, if the answer of the step S140 shows "YES", a step S150 is implemented to detect an element admittance, then followed by as step S160 to conduct the heater energizing control.

The heater energizing control corresponds to the element activation, and as the heater energizing control, an arbitrary control method is employable provided that it can maintain the element admittance at a desired target value. As one example, in a case in which the element temperature of the gas concentration sensor 100 is low and the element admittance is relatively low, the heater energizing is made through, for example, the full energizing control involving the duty ratio 100%. If the element temperature rises, the control duty ratio is calculated using a well-known feedback method such as PID control and the heater energizing is conducted on the basis of that duty ratio.

Secondly, referring to FIGS. 5 and 6, a description will be given hereinbelow of the A/F activation decision processing (the above-mentioned processing in the step S110 in FIG. 4) and the NOx activation decision processing (the aforesaid processing in the step S120 in FIG. 4).

Figure 5:
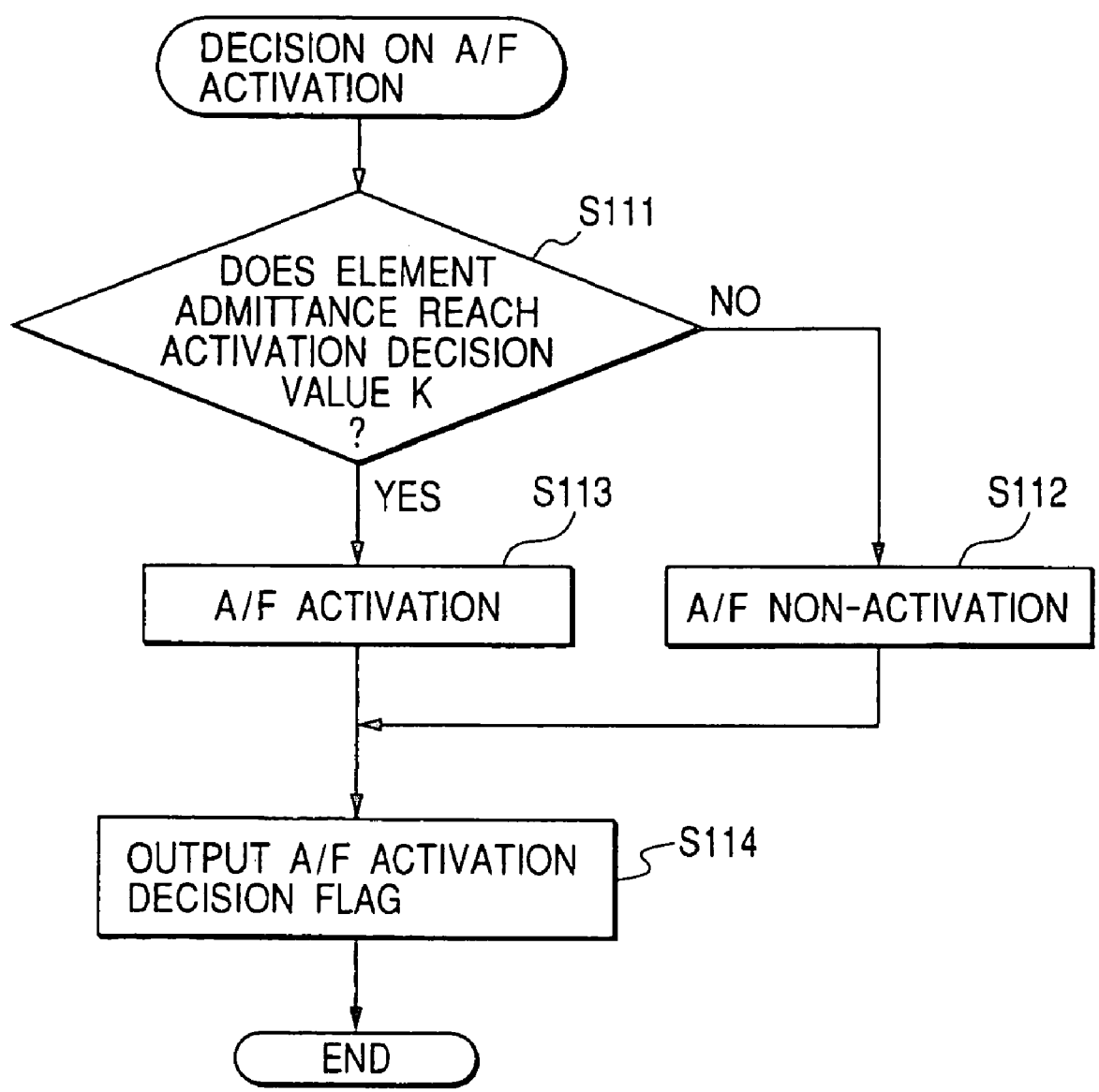
FIG. 5 is a flow chart showing an A/F activation decision processing according to the embodiment.

In FIG. 5, in a step S111, a decision is made as to whether or not the element admittance reaches a predetermined activation decision value K. The activation decision value K is determined on the basis of a target value of the element admittance and, for example, it is set at 40% of the target value. However, preferably, the determination on what percent of the target value the activation decision value K is set at is made in accordance with the degree of normalization of the pump cell current Ip with respect to an element admittance increase rate. In a case in which the normalization of the pump cell current relative to an increase in the element admittance is slow, the activation decision value K may be set at a value above 40% of the target value, or example, at 80% or 100%. On the other hand, in a case in which the normalization of the pump cell current relative to an increase in the element admittance is fast, the activation decision value K may be set at a value below 40% of the target value, or example, at 20% or 10%.

Returning again to FIG. 5, if the activation decision value K does not reach the activation decision value K because of the gas concentration sensor 100 being in the middle of the activation, the operational flow advances to a step S112 to make a decision indicative of the A/F non-activation (that is, pump cell non-activation). On the other hand, if the element admittance has reached the activation decision value K, the operational flow proceeds to a step S113 to make a decision indicative of the A/F activation (that is, pump cell activation).

Following this, in a step S114, an A/F activation decision flag indicative of the A/F activation or the A/F non-activation is outputted to the engine ECU or the like. At this time, if the A/F activation decision flag indicates the A/F activation (that is, the pump cell activation completion), the aforesaid A/F output in FIG. 4 is made effective. Otherwise, it is made invalid.

Figure 6:
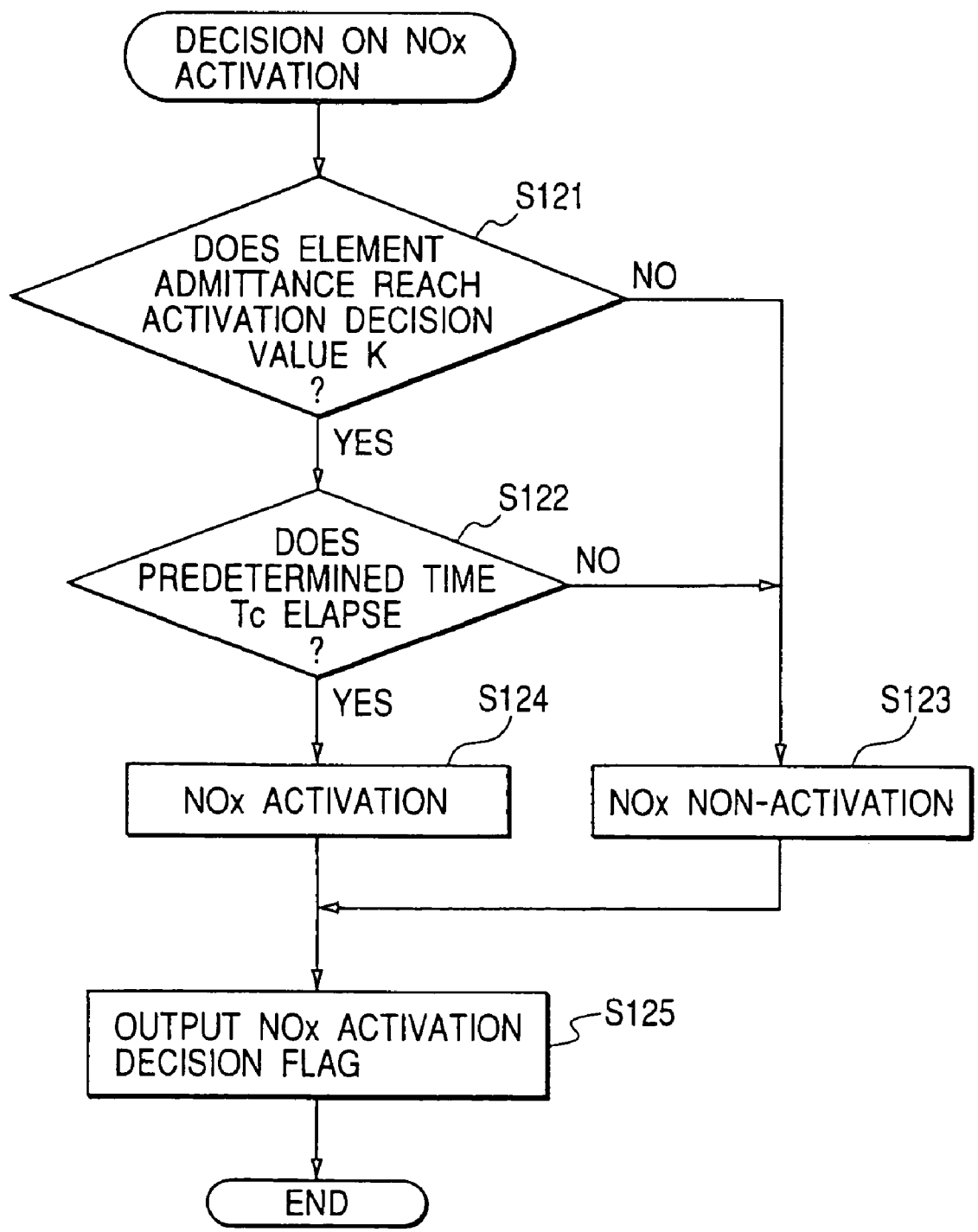
FIG. 6 is a flow chart showing an NOx activation decision processing according to the embodiment.

Furthermore, in FIG. 6, a step S121 is first implemented to make a decision as to whether or not the element admittance reaches a predetermined activation decision value K. That is, this processing, is for making a decision as to whether or not the A/F activation reaches completion, and is equal in meaning to a decision on "A/F activation completed?". After the arrival at the activation decision value K (that is, after the completion of A/F activation), the operational flow goes to a step S122 to make a decision as to whether a predetermined time Tc has elapsed after the arrival at the activation decision value K. In this case, the predetermined time Tc is determined on the basis of a time needed for emitting all the oxygen adsorbed onto the NOx active electrode of the sensor cell 130 (for example, in the case of a rhodium electrode, 2 minutes from the sensor starting). It is desirable that this predetermined time Tc is set in consideration of the surplus oxygen discharging capability of the pump cell 110, and if the pump cell electrode has a large area and the surplus oxygen discharging capability is high, since the normalization of the NOx output is made quickly, the predetermined time Tc may be set at a short time.

If the answer of the step S122 shows that the predetermined time Tc does not elapse yet, the operational flow advances to a step S123 to make a decision indicative of the NOx non-activation (that is, the sensor cell non-activation). On the other hand, if the predetermined time Tc has elapsed, the operational flow proceeds to a step S124 to make a decision indicative of the NOx activation (that is, the sensor cell activation).

Following this, in a step S125, an NOx activation decision flag indicative of the NOx activation or the NOx non-activation is outputted to the engine ECU or the like. At this time, if the NOx activation decision flag indicates the NOx activation (that is, the sensor cell activation completion), the NOx concentration output is made effective. Otherwise, it is made invalid.

Figure 7:
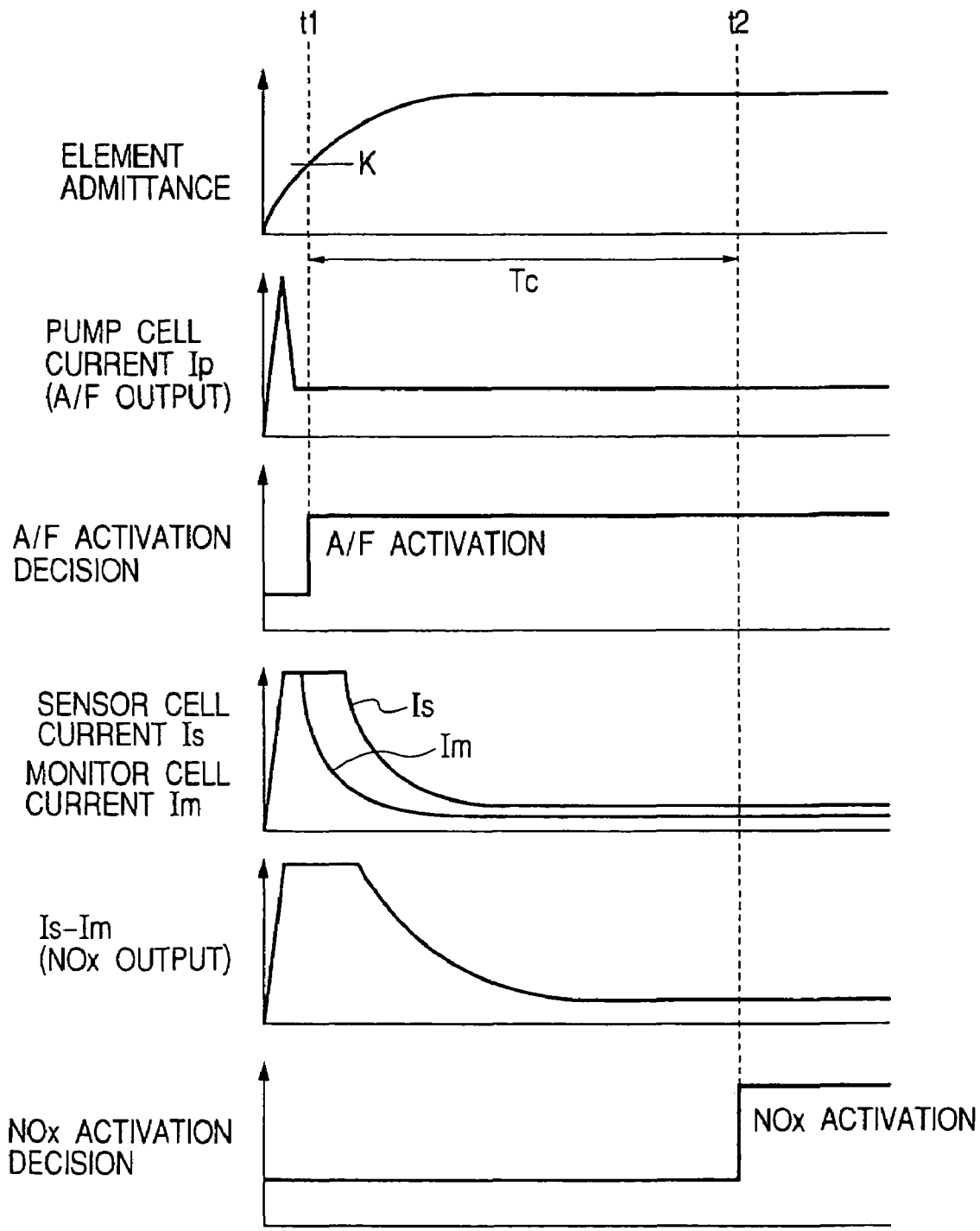
FIG. 7 is a time chart showing an activation operation at the start-up of a sensor according to the embodiment.

FIG. 7 is a time chart showing an activation operation at the start-up of the sensor.

When the heater energizing and sensor control start, the element temperature of the gas concentration sensor 100 rises gradually and the element admittance increases accordingly as shown in the illustration. In the pump cell 110, the surplus oxygen in the first chamber 144 is discharged from the start, and a large pump cell current Ip flows temporarily with the oxygen discharge. Moreover, when the surplus oxygen discharge comes to completion and the residual oxygen concentration in the first chamber 144 converges into a predetermined level, the pump cell current Ip becomes equable, thus providing a normal A/F output. In this case, additionally, in consideration of the behavior of the element admittance, it is seen that, before the element admittance converges into a target value, the pump cell current Ip takes a normal value. Concretely, at the time that the element admittance reaches approximately 20 to 40% of the target value, the pump cell current Ip takes a normal value. For this reason, the activation decision value K is set at 40% of the target value and a decision indicative of the A/F activation is made when the element admittance reaches the activation decision value K. That is, in FIG. 7, the A/F activation decision is made at the time (timing) t.

On the other hand, oxygen is adsorbed onto the rhodium which is a material for the electrode of the sensor cell 130 used as the NOx active element, and the oxygen is discharged after the start of the heater energizing and sensor control. For this reason, the sensor cell current Is shows a normal value until the oxygen discharge comes to completion and, hence, there is a need for the NOx concentration detection to wait for this time. Concretely, it takes about 2 minutes until the NOx concentration value reaches an accuracy of appropriately ±5 ppm. In particular, since the pump cell current Ip is on the order of mA while the sensor cell current Is or the monitor cell current Im is on the order of nA, a high accuracy is required with respect to the measurement of the sensor cell current Is or the monitor cell current Im. Accordingly, even if the A/F value is accurately detected at the aforesaid decision indicative of the A/F activation, for detecting the NOx concentration value with high accuracy, there is a need to further wait for the discharge of the surplus oxygen.

In FIG. 7, the decision indicative of the completion of the NOx activation is made at the time t2 at which the predetermined time Tc has elapsed from the A/F activation decision (from the timing t1).

At the times t1 and t2, the flag information indicative of the A/F activation and NOx activation is transmitted to the engine ECU and, after the flag transmission, the A/F value or the NOx concentration value is used for the control in the engine ECU. This prevents an unreliable output during the A/F non-activation or the NOx non-activation to be used in error. In this connection, it is also possible that the output of the A/F value or the NOx concentration value is inhibited until the A/F activation or the NOx activation reaches completion and the output of the A/F value or the NOx concentration value starts when the A/F activation or the NOx activation reaches completion.

As described above in detail, according to this embodiment, since the decision on the activation of the pump cell 110 and the decision on the activation of the sensor cell 130 are individually made in the middle of the activation of the gas concentration sensor 100, an appropriate decision is made on the activation of each cell and the use of the A/F value (oxygen concentration signal) or the NOx concentration value (specific gas concentration signal) starts at an appropriate timing. In particular, with respect to the pump cell 110, the decision on the activation completion can be made without waiting until the sensor cell 130 reaches the activation completion, which permits the use of the normal A/F value in early stages.

The present invention is not limited to the above-described embodiment, but, for example, the following is also acceptable.

Although in the above-described embodiment a decision indicative of the A/F activation completion is made when the element admittance reaches the activation decision value K (for example 40% of the target value) as described above with reference to FIG. 5, in a case in which the admittance value varies greatly and the activation decision value K cannot be set a fixed value such as 40% at which the pump cell current shows a normal value, it is also appropriate that the decision indicative of the A/F activation is made at the time that a predetermined time elapses after the element admittance reaches the activation decision value K.

In addition, it is also appropriate that the decision condition additionally includes the fact that, after the sensor starting, the pump cell current (first cell detection current) falls within a predetermined range. That is, a detection is made as to whether or not the pump cell current falls within a predetermined range (for example, below 4 mA before the convergence of the pump cell current) and a decision indicative of the A/F activation is made when the element admittance reaches the activation decision value K and the pump cell current falls within a predetermined range. This arrangement can enhance the accuracy of the A/F activation decision.

Still additionally, it is also appropriate that, depending on the element admittance (element resistance value), a decision indicative of the A/F activation is made at the time that a predetermined time (for example, approximately several tens ms) elapses from the start of the heater energizing.

Furthermore, although in the above-described embodiment a decision indicative of the completion of the NOx activation is made when the element admittance reaches the activation decision value K (that is, the A/F activation reaches completion) and the predetermined time Tc elapses therefrom as described above with reference to FIG. 6, it is also appropriate that the NOx activation decision condition additionally includes the fact that, after the sensor starting, the sensor cell current (second cell detection current) or the monitor cell current (third cell detection current) falls within a predetermined range. Still furthermore, it is also appropriate that to the NOx activation decision condition are added the fact that the NOx detection current (Is−Im) forming the subtraction result between the monitor cell current (corresponding to the offset error) and the sensor cell current falls within a predetermined range. This can improve the accuracy of the NOx activation decision.

In such a case, since the sensor cell current or the NOx detection current varies in current level in accordance with the engine operating state, the decision criterion on whether or not the current value falls within the predetermined range is set at a relatively large value. On the other hand, in the case of the monitor cell current, since the oxygen concentration in the chamber is controlled by the pump cell to be constant, the decision criterion can be further limited (for example, below 0.3 μA). This enables implementing the NOx activation decision more accurately.

It is also possible that the predetermined time Tc for the NOx activation detection is set variably in accordance with a sensor state in each case. For example, the oxygen adsorption quantity to the NOx active electrode is estimated and if the oxygen adsorption quantity is estimated to be small, the predetermined time Tc is shortened with respect to a maximum value (for example, 2 minutes). The oxygen adsorption quantity can be estimated on the basis of the time taken for the A/F activation or the engine warming-up state (water temperature at the start). According to this embodiment, the decision on the NOx activation (activation completion) can be made at a more optimum timing.

Although in the above-described embodiment the NOx concentration value is calculated on the basis of the NOx detection current (Is−Im) obtained by subtracting the monitor cell current (corresponding to the offset error) from the sensor cell current, it is also acceptable that the NOx concentration value is calculated on the basis of only the sensor cell current without using the monitor cell current. That is, the monitor cell current appears to the residual oxygen concentration in the chamber and, assuming that the residual oxygen concentration is maintained at a constant value by the pump cell, the offset error value included in the sensor cell current can be considered to be constant. Therefore, when the offset error is considered to be constant, the measurement of the monitor cell current becomes unnecessary. Accordingly, in the gas concentration sensor, the monitor cell becomes unessential and, hence, the present invention is also applicable to a gas concentration sensor comprising a pump cell and a sensor cell only.

Although in the above description of the embodiment the gas concentration sensor 100 has a construction shown in FIG. 2, the present invention is also applicable to other gas concentration sensors. Concrete examples to which the present invention is also applicable will be described hereinbelow.

Figure 8:
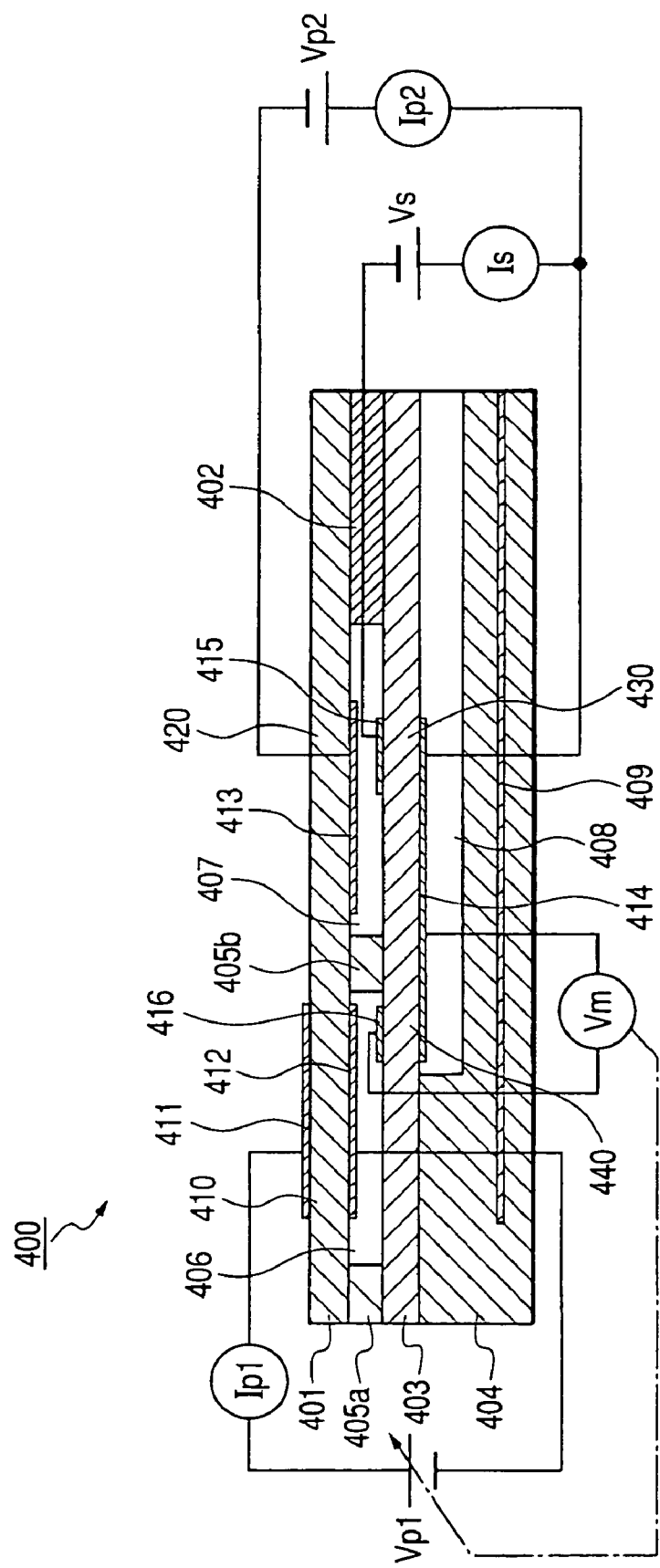
FIG. 8 is a cross-sectional view showing a different construction of the gas concentration sensor according to the embodiment.

In a gas concentration sensor generally designated at reference numeral 400 in FIG. 8, all sheet-like members, designated at reference numerals 401, 402, 403 and 404, are made of a solid electrolyte (for example, zirconia), and these solid electrolytes 401 to 404 are stacked in a vertical direction in the illustration. Between the solid electrolytes 401 and 403, a first chamber 406 and a second chamber 407 are defined with rate-determining layers 405a and 405b therebetween. An atmosphere passage 408 is formed by the solid electrolyte 404, and a heater 409 is buried in the same solid electrolyte 404.

In addition, the gas concentration sensor 400 is equipped with a first pump cell 410, a second pump cell 420, a sensor cell 430 and a monitor cell 440. A feature of this sensor 400 is that the coupling between these cells 410 to 440 is made by the coupling between the solid electrolytes. With this construction, in the first pump cell 410, a voltage Vp1 is applied between a pair of electrodes 411 and 412 to detect a first pump cell current Ip1 flowing at that time. In the second pump cell 420, a voltage Vp2 is applied between electrodes 413 and 414 to detect a second pump cell current Ip2 flowing at that time. In the sensor cell 430, a voltage Vs is applied between electrodes 414 and 415 to detect a sensor cell current Is flowing at that time. Moreover, in the monitor cell 440, an electromotive force signal Vm is detected between the electrode 414 and an electrode 416.

An exhaust gas is introduced through the rate-determining layer 405a into the first chamber 406. Most of oxygen in the exhaust gas is detected on the basis of the electromotive force signal Vm of the monitor cell 440, and the applied voltage Vp1 to the first pump cell 410 is controlled on the basis of this signal Vm, thereby discharging it from the electrode 411 to the external. The remaining gas passes through the rate-determining layer 405b and is then introduced into the second chamber 407. The residual oxygen of the gas is decomposed by an application of the voltage Vp2 in the second pump cell 420 and is then discharged to the atmosphere passage 408. Moreover, NOx of the gas is decomposed by an application of the voltage Vs in the sensor cell 430 and is then discharged to the atmosphere passage 408. An NOx concentration value is calculated on the basis of a sensor cell current Is flowing at that time. In the gas concentration sensor 400 shown in FIG. 8, the first pump cell 410 corresponds to a "first cell", the sensor cell 430 to a "second cell", and the second pump cell 420 to a "third cell".

In the gas concentration sensor 400 thus constructed, an element resistance value (element admittance or element impedance) can be detected any one of the cells 410 to 440.

In addition, a gas concentration sensor, generally designated at reference numeral 400, to which the present invention is also applicable is constructed as follows. That is, in FIG. 9, in a first pump cell 410, a voltage Vp1 is applied between a pair of electrodes 411 and 412 to detect a first pump cell current Ip1 flowing at that time. In a second pump cell 420, a voltage Vp2 is applied between electrodes 411 and 413 to detect a second pump cell current Ip2 flowing at that time. In a sensor cell 430, a voltage Vs is applied between electrodes 414 and 415 to detect a sensor cell current Is flowing at that time. Moreover, in a first monitor cell 450, an electromotive force signal Vm1 is detected between the electrodes 412 and 414, and in a second monitor cell 460, an electromotive force signal Vm2 is detected between the electrodes 413 and 414.

Figure 9:
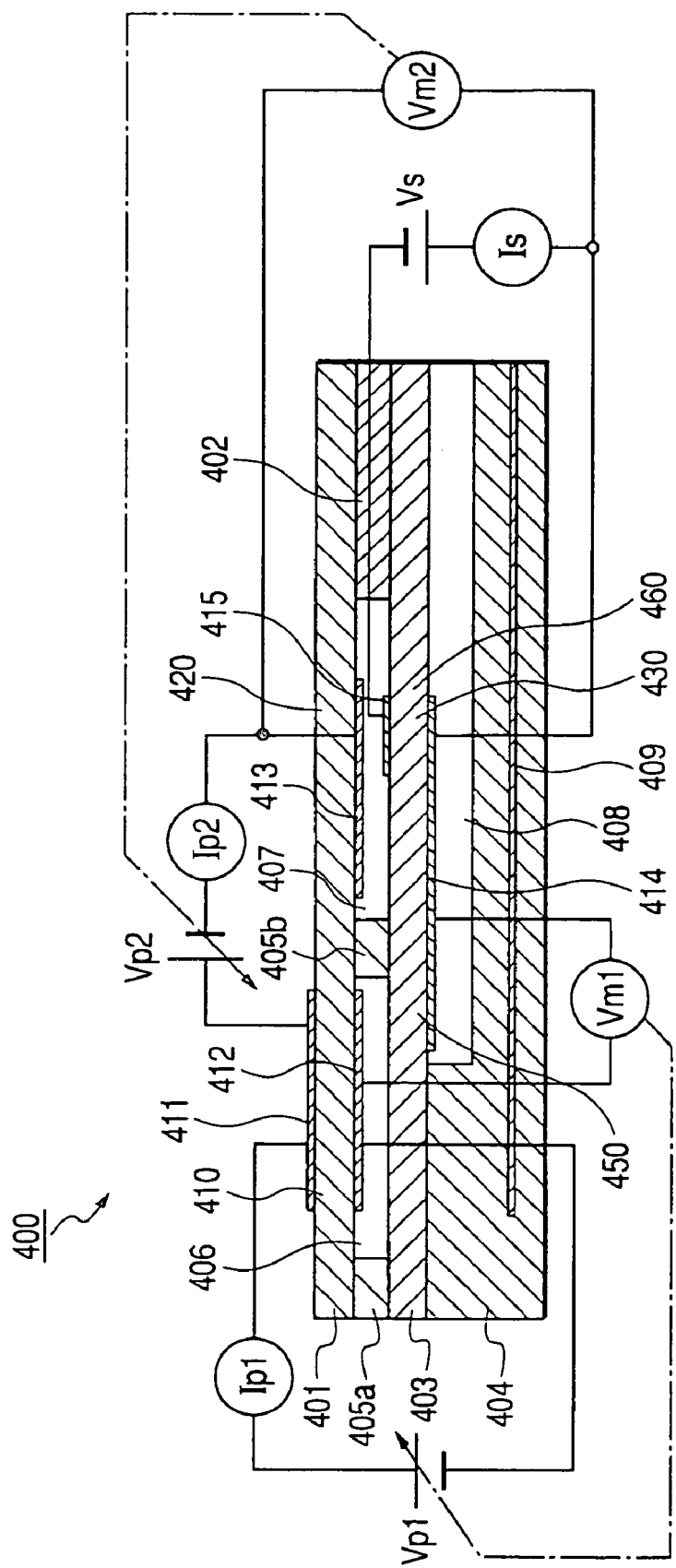
FIG. 9 is a cross-sectional view showing a different construction of the gas concentration sensor according to the embodiment.

In the gas concentration sensor 400 shown in FIG. 9, after an exhaust gas is introduced through a rate-determining layer 405a into a first chamber 406, most of oxygen of the exhaust gas is detected by an electromotive force signal V1 in the first monitor cell 450, and an applied voltage Vp1 to the first pump cell 410 is controlled in accordance with the signal Vm1, thereby discharging it from the electrode 411 to the external. The remaining gas passes through a rate-determining layer 405b and then enters a second chamber 407. The residual oxygen of the gas is detected on the basis of an electromotive force signal Vm2 of the second monitor cell 460, and an applied voltage Vp2 to the second pump cell 420 is controlled in accordance with the signal Vm2, thus accomplishing the discharge from the electrode 411 to the external. Moreover, NOx of the gas is decomposed by an application of a voltage Vs in the sensor cell 430 and is then discharged to the atmosphere passage 408. An NOx concentration value is calculated on the basis of a sensor cell current Is flowing at that time. In the gas concentration sensor 400 shown in FIG. 9, the first pump cell 410 corresponds to a "first cell", the sensor cell 430 to a "second cell", and the second pump cell 420 to a "third cell".

Furthermore, in addition to the gas concentration sensors whereby an NOx concentration is detectable, the present invention is also applicable to gas concentration sensors which can detect an HC concentration or a CO concentration as a specific gas component. In this case, the surplus oxygen of a gas to be detected is discharged by a pump cell and, in a sensor cell, of the gas after the discharge of the surplus oxygen, HC or CO is decomposed to detect an HC concentration or a CO concentration. Still furthermore, the present invention is also applicable to gas concentration detecting apparatus other than for cars, and to a case of a detection of a gas other than the exhaust gas.

It should be understood that the present invention is not limited to the above-described embodiment, and that it is intended to cover all changes and modifications of the embodiment of the invention herein which do not constitute departures from the spirit and scope of the invention.

What is claimed is:

1. A gas concentration detecting apparatus comprising:
a gas sensor further comprising:
a first cell for detecting a concentration of oxygen in a measurement gas, the first cell having a first chamber and a pair of first electrodes, discharging or pumping in oxygen contained in the measurement gas introduced from an external space into the first chamber to generate a pumped measurement gas which contains an excessive oxygen and to output a first electric current indicating the concentration of oxygen in the measurement gas when a first electric voltage is applied between the pair of the first electrodes; and
a second cell for detecting a concentration of a specific gas in the pumped measurement gas, the second cell having a second chamber and a pair of second electrodes and decomposing the specific gas contained in the pumped measurement gas which is generated by the first cell and is introduced from the first chamber into the second chamber to output a second electric current indicating a concentration of the specific gas in the measurement gas when a second electric voltage is applied between the pair of the second electrodes; and
a controller that determines a completion of activation of the first cell for allowing to start making use of the first electric current at a first time moment at which a first predetermined period of time elapses after the electric power has been started to be supplied to the first and the second cells to activate at least the one of the first cell and the second cell, and determines a completion of activation of the second cell for allowing to start making use of the second electric current when the second electric current flowing in the second cell of the gas sensor is fallen into a predetermined range and when a predetermined time elapses.

2. The gas concentration detecting apparatus according to claim 1, wherein the controller determines the second time moment at which the controller determines that the activation of the second cell is completed when a second predetermined period of time elapses after the activation of the first cell has been completed.

3. The gas concentration detecting apparatus according to claim 2, wherein the second predetermined period of time is determined on the basis of a time needed for discharging all oxygen absorbed onto one of the second electrodes of said second cell.

4. The gas concentration detecting apparatus according to claim 1, wherein the first cell comprises a first solid electrolyte element which is sandwiched between the first electrodes, and the second cell comprises a second solid electrolyte element which is sandwiched between the second electrodes, further comprising:
an element resistance monitor for monitoring a resistance value of at least one of the first and second solid electrolyte element to control a degree of activation of the cell in order to keep the resistance value of the corresponding solid electrolyte element at a first predetermined target value after starting energization of the gas concentration sensor,
wherein the controller determines the completion of the activation of the first cell for allowing to start making use of the first electric current when the monitored resistance value of the solid electrolyte element which is monitored by the element resistance monitor becomes a second predetermined target value.

5. The gas concentration detecting apparatus according to claim 4, wherein the controller determines a completion of activation of the first cell for allowing to start making use of the first electric current, when the monitored resistance value of the solid electrolyte element which is monitored by the element resistance monitor is within a predetermined range, and a predetermined time elapses after the monitored resistance value of the solid electrolyte element which is monitored by the element resistance monitor has been within the predetermined range.

6. The gas concentration detecting apparatus according to claim 4, wherein the controller determines a completion of activation of the first cell for allowing to start making use of the first electric current, when the monitored resistance value of the solid electrolyte element which is monitored by the element resistance monitor becomes a second predetermined target value, and a predetermined time elapses after the monitored resistance value of the first solid electrolyte element which is monitored by the element resistance monitor has become the second predetermined target value.

7. The gas concentration detecting apparatus according to claim 1, further comprising:
a heater that heats up at least one of the first cell and the second cell to activate the one of the first cell and the second cell when an electric power is supplied to the heater, and wherein the controller that determines the completion of activation of the first cell for allowing to start making use of the first electric current at a first time moment at which a predetermined period of time elapses after the electric power has been started to be supplied to the heater to activate at least the one of the first cell and the second cell.

8. The gas concentration detecting apparatus according to claim 1, wherein the predetermined period of time is determined on the basis of a time needed for discharging all oxygen absorbed onto one of the second electrodes of said second cell.

9. The apparatus according to claim 1, wherein
the first electrodes of the first cell is reactively inactive with respect to the specific gas, and
the second electrodes of the second cell is reactively active with respect to the specific gas.

10. The apparatus according to claim 1, further comprising:
a third cell for detecting a residual oxygen concentration of said measuring gas after passing through said first cell,
wherein an amplitude of said first voltage to be applied to said first cell from the power supply is variably controlled on the basis of a detection result in said third cell.

11. A gas concentration detecting apparatus comprising:
a gas sensor further comprising:
a first cell for detecting a concentration of oxygen in a measurement gas, the first cell having a first chamber and a pair of first electrodes, discharging or pumping in oxygen contained in the measurement gas introduced from an external space into the first chamber to generate a pumped measurement gas which contains an excessive oxygen and to output a first electric current indicating the concentration of oxygen in the measurement gas when a first electric voltage is applied between the pair of the first electrodes;
a second cell for detecting a concentration of a specific gas in the pumped measurement gas, the second cell having a second chamber and a pair of second electrodes and decomposing the specific gas contained in the pumped measurement gas which is generated by the first cell and is introduced from the first chamber into the second chamber to output a second electric current indicating a concentration of the specific gas in the measurement gas when a second electric voltage is applied between the pair of the second electrodes; and a third cell for detecting a residual oxygen concentration of said measuring gas after passing through said first cell, the third cell outputting a third electric current indicating the residual oxygen concentration in the measurement gas when a third electric voltage is applied thereto; and a controller that determines a completion of activation of the first cell for allowing to start making use of the first electric current at a first time moment at which a first predetermined period of time elapses after the electric power has been started to be supplied to at least the first and the second cells to activate at least the one of the first cell and the second cell, and determines a completion of activation of the second cell for allowing to start making use of the second electric current when the third electric current flowing in the third cell of the gas sensor is fallen into a predetermined range and when a predetermined time elapses.

12. The gas concentration detecting apparatus according to claim 11, wherein the first cell comprises a first solid electrolyte element which is sandwiched between the first electrodes, the second cell comprises a second solid electrolyte element which is sandwiched between the second electrodes, and third cell comprises a third solid electrolyte element, further comprising:

an element resistance monitor for monitoring a resistance value of at least one of the first, second, and third solid electrolyte element to control a degree of activation of the cell in order to keep the resistance value of the corresponding solid electrolyte element at a first predetermined target value after starting energization of the gas concentration sensor, wherein the controller determines the completion of the activation of the first cell for allowing to start making use of the first electric current when the monitored resistance value of the solid electrolyte element which is monitored by the element resistance monitor becomes a second predetermined target value.

13. The gas concentration detecting apparatus according to claim 12, wherein the controller determines a completion of activation of the first cell for allowing to start making use of the first electric current, when the monitored resistance value of the solid electrolyte element which is monitored by the element resistance monitor is within a predetermined resistance range, and a predetermined time elapses after the monitored resistance value of the solid electrolyte element which is monitored by the element resistance monitor has been within the predetermined range.

14. The gas concentration detecting apparatus according to claim 12, wherein the controller determines a completion of activation of the first cell for allowing to start making use of the first electric current, when the monitored resistance value of the solid electrolyte element which is monitored by the element resistance monitor becomes a second predetermined target value, and a predetermined time elapses after the monitored resistance value of the first solid electrolyte element which is monitored by the element resistance monitor has become the second predetermined target value.

15. The gas concentration detecting apparatus according to claim 11, further comprising:

a heater that heats up at least one of the first cell and the second cell to activate the one of the one of the first, second, and third cell when an electric power is supplied to the heater, and wherein the controller that determines the completion of activation of the first cell for allowing to start making use of the first electric current at a first time moment at which a predetermined period of time elapses after the electric power has been started to be supplied to the heater to activate at least the one of the first, second, and third cell.

* * * * *